United States Patent
Kim et al.

(10) Patent No.: US 8,663,110 B2
(45) Date of Patent: Mar. 4, 2014

(54) PROVIDING AN OPTIMAL ULTRASOUND IMAGE FOR INTERVENTIONAL TREATMENT IN A MEDICAL SYSTEM

(75) Inventors: Chul An Kim, Seoul (KR); Young Seuk Song, Seoul (KR); Dong Gyu Hyun, Seoul (KR)

(73) Assignee: Samsung Medison Co., Ltd., Gangwon-Do (KR)

( * ) Notice: Subject to any disclaimer, the term of this patent is extended or adjusted under 35 U.S.C. 154(b) by 156 days.

(21) Appl. No.: 13/108,429

(22) Filed: May 16, 2011

(65) Prior Publication Data

US 2012/0123249 A1    May 17, 2012

(30) Foreign Application Priority Data

Nov. 17, 2010    (KR) ........................ 10-2010-0114331

(51) Int. Cl.
*A61B 8/00* (2006.01)
(52) U.S. Cl.
USPC ............ 600/437; 600/424; 600/443; 600/461
(58) Field of Classification Search
USPC ........................................ 600/437, 424, 443
See application file for complete search history.

(56) References Cited

U.S. PATENT DOCUMENTS

| | | | |
|---|---|---|---|
| 5,967,985 A | 10/1999 | Hayakawa | |
| 5,967,991 A | 10/1999 | Gardineer et al. | |
| 6,336,899 B1 * | 1/2002 | Yamazaki | 600/443 |
| 2002/0173719 A1 | 11/2002 | Zhao et al. | |
| 2003/0135119 A1 | 7/2003 | Lee et al. | |
| 2006/0241451 A1 * | 10/2006 | Nakaya et al. | 600/443 |
| 2008/0077009 A1 | 3/2008 | Lee et al. | |
| 2008/0091106 A1 | 4/2008 | Kim et al. | |
| 2012/0101370 A1 * | 4/2012 | Razzaque et al. | 600/424 |

FOREIGN PATENT DOCUMENTS

| | | |
|---|---|---|
| EP | 0 453 251 A1 | 10/1991 |
| EP | 1 323 380 A2 | 7/2003 |
| EP | 2 215 969 A1 | 8/2010 |
| JP | 2008-237787 | 10/2008 |
| KR | 10-2003-0058423 | 7/2003 |
| KR | 10-2008-0028106 | 3/2008 |

(Continued)

OTHER PUBLICATIONS

Korean Office Action issued in Korean Patent Application No. 10-2010-0114331 dated Apr. 10, 2012.

(Continued)

*Primary Examiner* — Baisakhi Roy
(74) *Attorney, Agent, or Firm* — McDermott Will & Emery LLP

(57) ABSTRACT

Embodiments for providing an optimal ultrasound image for interventional treatment in a medical system are disclosed. In one embodiment, by way of non-limiting example, a medical system comprises: a medical device that is inserted into a target object and configured to remove a lesion within the target object; an ultrasound data acquisition unit configured to transmit and receive ultrasound signals to and from the target object to output ultrasound data; and a processing unit in communication with the ultrasound data acquisition unit, the processing unit being configured to form a plurality of ultrasound images based on the ultrasound data and perform an image processing upon each of the ultrasound images to detect a position of the medical device.

8 Claims, 5 Drawing Sheets

(56) References Cited

FOREIGN PATENT DOCUMENTS

| KR | 10-2008-0034664 | 4/2008 |
| WO | WO 99/16352 A1 | 4/1999 |
| WO | WO 2004/019799 A2 | 3/2004 |
| WO | WO 2004/082749 A2 | 9/2004 |
| WO | WO 2004/086082 A1 | 10/2004 |
| WO | WO 2009/069038 A1 | 6/2009 |

OTHER PUBLICATIONS

Extended European Search Report issued in European Patent Application No. 11165987.6, dated Mar. 26, 2012.
Korean Office Action, issued in Korean Patent Application No. 10-2010-0114331, dated Oct. 31, 2011.

* cited by examiner

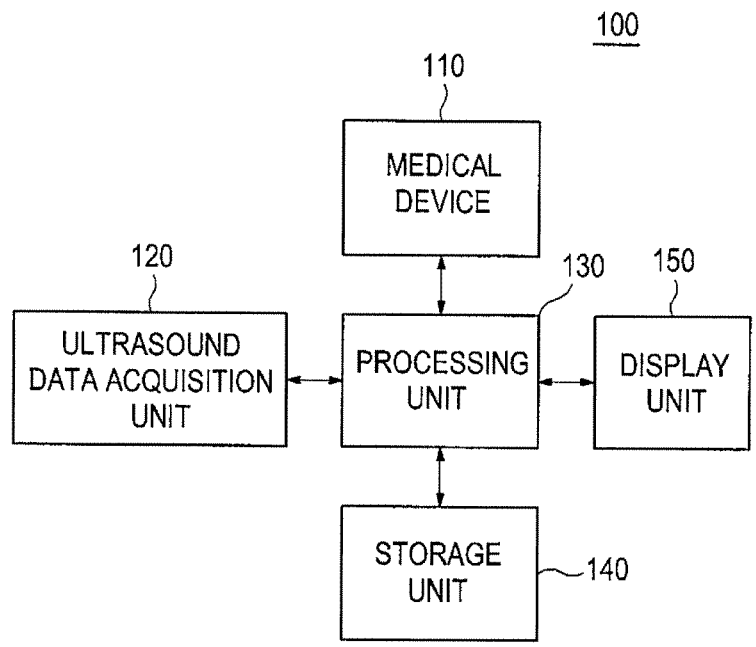
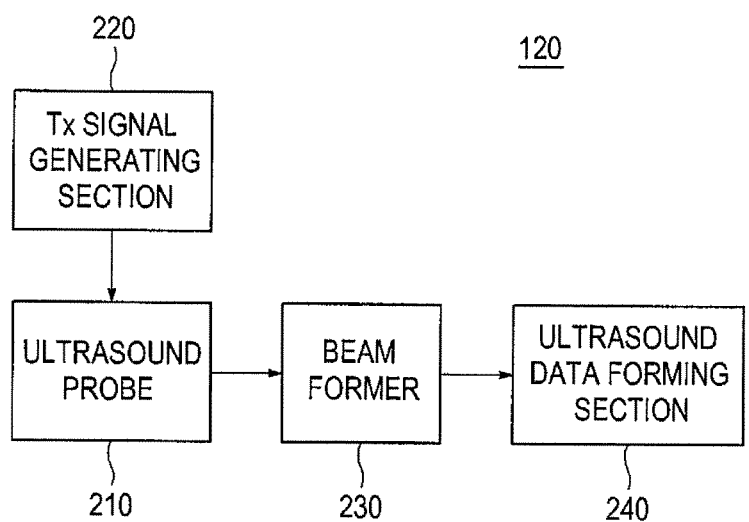

PROVIDING AN OPTIMAL ULTRASOUND IMAGE FOR INTERVENTIONAL TREATMENT IN A MEDICAL SYSTEM

CROSS-REFERENCE TO RELATED APPLICATIONS

The present application claims priority from Korean Patent Application No. 10-2010-0114331 filed on Nov. 17, 2010, the entire subject matter of which is incorporated herein by reference.

TECHNICAL FIELD

The present disclosure generally relates to medical systems, and more particularly to providing an optimal ultrasound image for interventional treatment in a medical system.

BACKGROUND

Surgical treatment using a medical needle such as ablator or biopsy has recently become popular due to relatively small incisions made in such a procedure. The surgical treatment is performed by inserting the medical needle into an internal region of a human body while referring to an internal image of the human body. Such surgical treatment, which is performed while observing internal organs of the human body with the help of a diagnostic imaging system, is referred to as an interventional treatment. The interventional treatment is performed by directing the medical needle to a lesion to be treated or examined through a skin with reference to images during the treatment. The images are acquired by employing a computerized tomography (CT) scanner, which is generally used in a radiology department, or a magnetic resonance imaging (MRI) system. Compared to a normal surgical treatment requiring relatively wide incisions to open the lesion, the interventional treatment has the advantages of low costs and obtaining effective operation results. This is because general anesthesia is not necessary for the interventional treatment and patients are subjected to less pain while benefiting from rapid recovery.

However, it is difficult to obtain such images in real time by using the CT scanner or the MRI system. Especially, when the interventional treatment is performed by using the CT scanner, both the patient and the operator are exposed to radiation for quite a long time. However, when the interventional treatment is performed by using an ultrasound diagnostic system, the images can be obtained in real time without affecting the human body. But, there is a problem since it is difficult to accurately recognize the lesion as well as the medical device (i.e., a needle) in the ultrasound image obtained by using the ultrasound system.

SUMMARY

Embodiments for providing an optimal ultrasound image for interventional treatment in a medical system are disclosed herein. In one embodiment, by way of non-limiting example, a medical system comprises: a medical device inserted into a target object and configured to remove a lesion within the target object; an ultrasound data acquisition unit configured to transmit and receive ultrasound signals to and from the target object to output ultrasound data; and a processing unit in communication with the ultrasound data acquisition unit, the processing unit being configured to form a plurality of ultrasound images based on the ultrasound data and perform an image processing upon each of the ultrasound images to detect a position of the medical device.

In another embodiment, there is a method of providing an ultrasound image for interventional treatment, comprising: a) inserting a medical device including a needle into a target object; b) transmitting and receiving ultrasound signals to and from the target object to output ultrasound data; c) forming a plurality of ultrasound images based on the ultrasound data; and d) performing an image processing upon each of the ultrasound images to detect a position of the needle.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIG. 1 is a block diagram showing an illustrative embodiment of a medical system.

FIG. 2 is a block diagram showing an illustrative embodiment of an ultrasound data acquisition unit.

DETAILED DESCRIPTION

Figure 3:
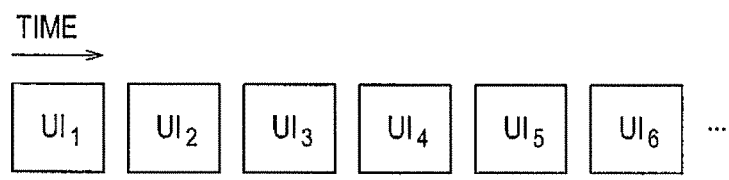
FIG. 3 is a schematic diagram showing an example of acquiring ultrasound data corresponding to a plurality of ultrasound images.

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

First Embodiment

FIG. 1 is a block diagram showing an illustrative embodiment of a medical system. As depicted therein, the medical system 100 may include a medical device 110. The medical device 110 may include a needle (not shown) for removing the lesion of a living body and a vibration applying section (not shown) for applying vibration to the needle. However, it should be noted herein that the medical device 110 may not be limited thereto. The living body may include a plurality of target objects (e.g., blood vessels, a heart, a lesion, etc.).

The medical system 100 may further include an ultrasound data acquisition unit 120. The ultrasound data acquisition unit 120 may be configured to transmit and receive ultrasound signals to and from the living body and output ultrasound data.

FIG. 2 is a block diagram showing the ultrasound data acquisition unit 120 in accordance with the first embodiment. Referring to FIG. 2, the ultrasound data acquisition unit 120 may include an ultrasound probe 210, a transmitting section ("Tx signal generating section") 220, a receiving section ("beam former") 230 and an ultrasound data forming section 240.

The ultrasound probe 210 may include a plurality of elements (not shown) for reciprocally converting between ultrasound signals and electrical signals. The ultrasound probe 210 may be configured to transmit ultrasound signals to the living body based on each of scanlines (not shown). The ultrasound probe 210 may further receive ultrasound signals (i.e., ultrasound echo signals) from the living body and output the received signals. The received signals may be analog signals. The ultrasound probe 210 may include a convex probe, a linear probe and the like.

The Tx signal generating section 220 may be configured to control the transmission of the ultrasound signals. The Tx signal generating section 220 may further generate electrical signals ("Tx signals") in consideration of the elements and focal points. The Tx signals may be low frequency (e.g., 2~5 MHz) Tx signals or high frequency (e.g., more than 10 MHz) Tx signals.

For example, the Tx signal generating section 220 may generate the Tx signals for obtaining each of a plurality of ultrasound images $UI_i$ ($1 \leq i$) as shown in FIG. 3, sequentially. Thus, the ultrasound probe 210 may convert the Tx signals provided from the Tx signal generating section 220 into the ultrasound signals, transmit the ultrasound signals to the living body and receive the ultrasound echo signals from the living body to thereby output electrical signals ("the received signals").

The beam former 230 may be configured to convert the received signals provided from the ultrasound probe 210 into digital signals. The beam former 230 may further apply delays to the digital signals in consideration of the elements and the focal points to output digital receive-focused signals.

The ultrasound data forming section 240 may be configured to form ultrasound data corresponding to the ultrasound images based on the digital receive-focused signals provided from the beam former 230. The ultrasound data forming section 240 may be further configured to perform signal processing (e.g., gain control, etc) upon the digital receive-focused signals.

Referring back to FIG. 1, the medical system 100 may further include a processing unit 130 in communication with the medical device 110 and the ultrasound data acquisition unit 120. The processing unit 130 may include a central processing unit, a microprocessor or a graphic processing unit. However, it should be noted herein that the processing unit 130 may not be limited thereto.

Figure 4:
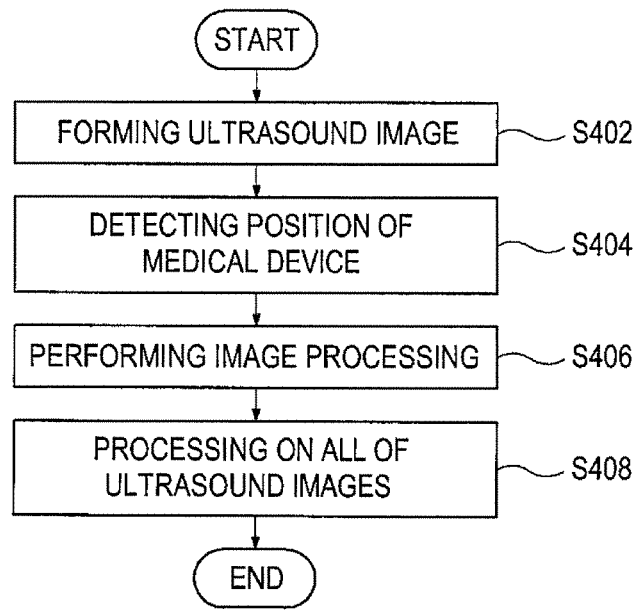
FIG. 4 is a flow chart showing a process of forming an optimal ultrasound image for interventional treatment in accordance with a first embodiment.

FIG. 4 is a flow chart showing a process of forming an optimal ultrasound image for interventional treatment in accordance with the first embodiment. As explained above, the medical device including the needle is inserted into the target object, and then the ultrasound data are obtained by transmitting and receiving ultrasound signals to and from the target object. The processing unit 130 may be configured to form the ultrasound image UI; based on the ultrasound data provided from the ultrasound data acquisition unit 120, at step S402 in FIG. 4.

The processing unit 130 may be configured to perform motion tracking between the ultrasound image $U_{i-1}$ and the ultrasound image $UI_i$ to detect a position of the medical device 110 from the ultrasound image $UI_i$, at step S404 in FIG. 4. The methods of performing the motion tracking are well known in the art. Thus, they have not been described in detail so as not to unnecessarily obscure the present invention.

The processing unit 130 may be configured to perform image processing for enhancing image quality upon the ultrasound image $UI_i$ based on the detected position, at step S406 of FIG. 4. The methods of enhancing the image quality are well known in the art. Thus, they have not been described in detail so as not to unnecessarily obscure the present invention.

The processing unit 130 may be configured to continuously perform the process upon all of the ultrasound images while performing the interventional treatment, as mentioned above, at step S408 in FIG. 4.

Referring back to FIG. 1, the medical system 100 may further include a storage unit 140. The storage unit 140 may store the ultrasound data acquired by the ultrasound data acquisition unit 120. The storage unit 140 may further store the ultrasound images formed by the processing unit 130.

The medical system 100 may further include a display unit 150. The display unit 150 may display the ultrasound images formed by the processing unit 130. The display unit 150 may further display the ultrasound images image-processed by the processing unit 130. The display unit 150 may include a cathode ray tube, a liquid crystal display, an organic light emitting diode and the like.

Second Embodiment

Referring to FIG. 1, the medical device 110 may include the needle (not shown for removing the lesion of the living body.

The ultrasound data acquisition unit 120 may include the ultrasound probe 210, the Tx signal generating section 220, the receiving section 230 and an ultrasound data forming section 240, as shown in FIG. 2.

The ultrasound probe 210 may include the plurality of elements (not shown) for reciprocally converting between ultrasound signals and electrical signals. The ultrasound probe 210 may be configured to transmit ultrasound signals to the living body based on each of the scanlines (not shown). The ultrasound probe 210 may further receive the ultrasound echo signals from the living body and output the received signals. The received signals may be analog signals.

The Tx signal generating section 220 may be configured to control transmission of the ultrasound signals. The Tx signal generating section 220 may be further configured to generate electrical signals ("Tx signals") for obtaining ultrasound images in consideration of the elements and focal points. In this embodiment, the Tx signal generating section 220 may be configured to form Tx signals for obtaining a reference ultrasound image, which does not steer the scanlines, and Tx signals for obtaining a plurality of sub ultrasound images, which electronically steer the scanlines in different steering angles.

Figure 5:
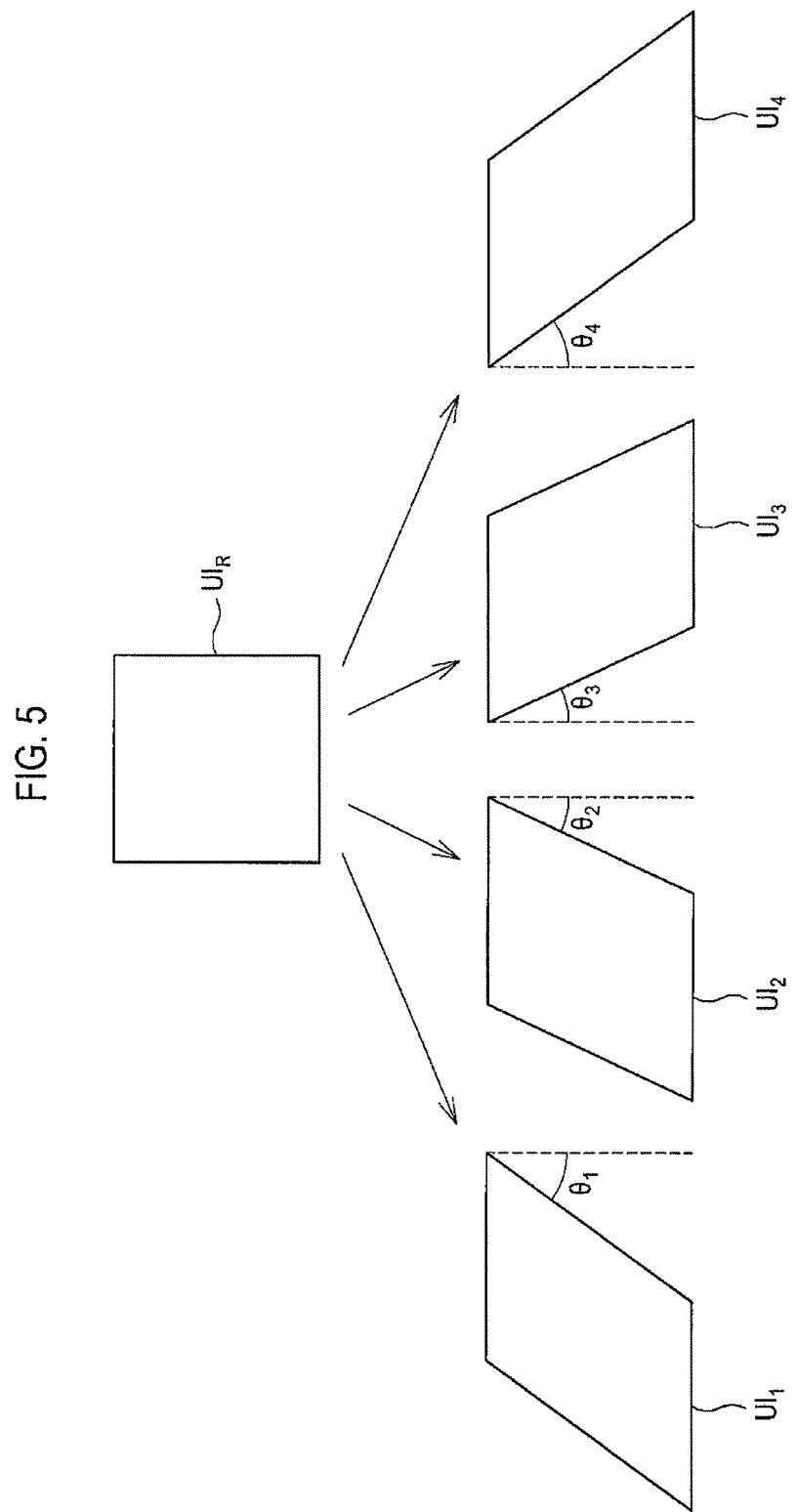
FIG. 5 is a schematic diagram showing an example of a reference ultrasound image and a plurality of sub ultrasound images in accordance with a second embodiment.

For example, the Tx signal generating section 220 may form first Tx signals for obtaining a reference ultrasound image $UI_R$, which does not steer the scanlines (not shown), as shown in FIG. 5. Thus, the ultrasound probe 210 may convert the first Tx signals provided from the Tx signal generating section 220 into ultrasound signals, transmit the ultrasound signals to the living body, and receive ultrasound echo signals from the living body to thereby output first received signals. The Tx signal generating section 220 may further generate second Tx signals for obtaining a first sub ultrasound image $SUI_1$, which electronically steers the scanlines in a first steering angle $\theta_1$, as shown in FIG. 5. As such, the ultrasound probe 210 may further convert the second Tx signals provided from the Tx signal generating section 220 into ultrasound signals, transmit the ultrasound signal to the living body, and receive ultrasound echo signals from the living body to thereby output second received signals. The Tx signal generating section 220 may further generate third Tx signals for obtaining a second sub ultrasound image $SUI_2$, which electronically steers the scanlines in a second steering angle $\theta_2$, as shown in FIG. 5. Thus, the ultrasound probe 210 may further convert the third Tx signals provided from the Tx signal generating section 220 into ultrasound signals, transmit the ultrasound signal to the living body, and receive ultrasound echo signals from the living body to thereby output third received signals. The Tx signal generating section 220 may further generate fourth Tx signals for obtaining a third sub ultrasound image $SUI_S$, which electronically steers the scanlines in a third steering angle $\theta_3$, as shown in FIG. 5. Thus, the ultrasound probe 210 may further convert the fourth Tx signals provided from the Tx signal generating section 220 into ultrasound signals, transmit the ultrasound signal to the living body, and receive ultrasound echo signals from the living body to thereby output fourth received signals. The Tx signal generating section 220 may further generate fifth Tx signals for obtaining a fourth sub ultrasound image $SUI_4$ which electronically steers the scanlines in a fourth steering angle $\theta_4$, as shown in FIG. 5. Thus, the ultrasound probe 210 may further convert the fifth Tx signals provided from the Tx signal generating section 220 into ultrasound signals, transmit the ultrasound signal to the living body, and receive ultrasound echo signals from the living body to thereby output fifth received signals.

The beam former 230 may be configured to convert the received signals provided from the ultrasound probe 210 into digital signals. The beam former 230 may be further configured to apply delays to the digital signals in consideration of the elements and the focal points to output digital receive-focused signals.

For example, the beam former 230 may convert the first received signals provided from the ultrasound probe 210 into first digital signals. The beam former 230 may further apply delays to the first digital signals in consideration of the elements and the focal points to output first digital receive-focused signals. Also, the beam former 230 may convert the second received signals provided from the ultrasound probe 210 into second digital signals. The beam former 230 may further apply delays to the second digital signals in consideration of the elements and the focal points to output second digital receive-focused signals. Also, the beam former 230 may convert the third received signals provided from the ultrasound probe 210 into third digital signals. The beam former 230 may further apply delays to the third digital signals in consideration of the elements and the focal points to output third digital receive-focused signals. Also, the beam former 230 may convert the fourth received signals provided from the ultrasound probe 210 into fourth digital signals. The beam former 230 may further apply delays to the fourth digital signals to output fourth digital receive-focused signals. Also, the beam former 230 may convert the fifth received signals provided from the ultrasound probe 210 into fifth digital signals. The beam former 230 may further apply delays to the fifth digital signals to output fifth digital receive-focused signals.

The ultrasound data forming section 240 may be configured to form ultrasound data based on the digital receive-focused signals provided from the beam former 230. The ultrasound data may include radio frequency data. The ultrasound data forming section 240 may further perform signal processing (e.g., gain control, etc) upon the digital receive-focused signals.

For example, the ultrasound data forming section 240 may form first ultrasound data corresponding to the reference ultrasound image $UI_R$ based on the first digital receive-focused signals. The ultrasound data forming section 240 may further form second ultrasound data corresponding to the first sub ultrasound image $SUI_1$ based on the second digital receive-focused signals. The ultrasound data forming section 240 may further form third ultrasound data corresponding to the second sub ultrasound image $SUI_2$ based on the third digital receive-focused signals. The ultrasound data forming section 240 may further form fourth ultrasound data corresponding to the third sub ultrasound image $SUI_3$ based on the fourth digital receive-focused signals. The ultrasound data forming section 240 may further form fifth ultrasound data corresponding to the fourth sub ultrasound image $SUI_4$ based on the fifth digital receive-focused signals.

Figure 6:
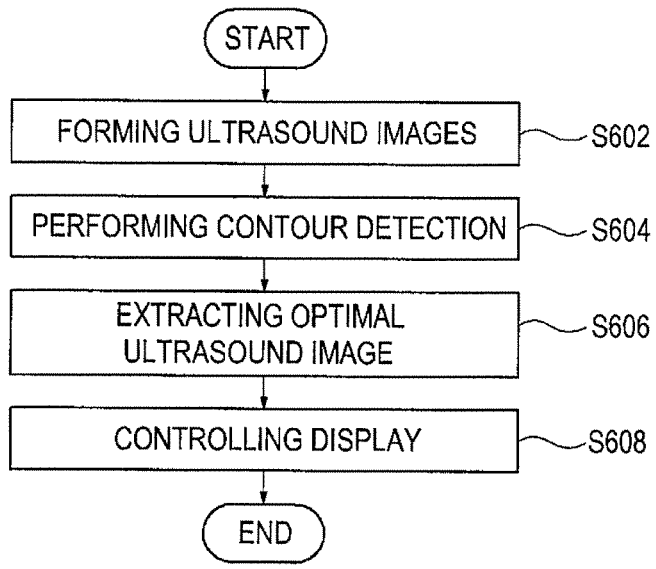
FIG. 6 is a flow chart showing a process of forming an optimal ultrasound image for interventional treatment in accordance with the second embodiment.

FIG. 6 is a flow chart showing a process of forming an optimal ultrasound image for interventional treatment in accordance with the second embodiment. The processing unit 130 may be configured to form ultrasound images based on the ultrasound data provided from the ultrasound data acquisition unit 120, at step S602 in FIG. 6. For example, the processing unit 130 may form the reference ultrasound image $UI_R$ based on the first ultrasound data provided from the ultrasound data acquisition unit 120. The processing unit 130 may further form the first sub ultrasound image $SU_1$ to the fourth sub ultrasound image $SUI_4$ based on the second ultrasound data to fifth ultrasound data provided from the ultrasound data acquisition unit 120.

The processing unit 130 may be configured to perform a contour detection upon each of the sub ultrasound images to detect the contour of the medical device 110, at step S604 in FIG. 6. The methods of performing the contour detection are well known in the art. Thus, they have not been described in detail so as not to unnecessarily obscure the present invention.

The processing unit 130 may be configured to compare the detected coutours from each of the sub ultrasound images to extract an optimal sub ultrasound image from the sub ultrasound images based on the detected contour, at step S606 in FIG. 6. For example, the processing unit 130 may detect a sub ultrasound image having the contour of a maximum brightness value from the sub ultrasound images, and extract the detected sub ultrasound image as the optimal sub ultrasound image.

The processing unit 130 may be configured to control display of the reference ultrasound image and the optimal sub ultrasound image, at step S608 in FIG. 6. For example, the processing unit 130 may control that the reference ultrasound image and the extracted sub ultrasound image are displayed in dual form.

Referring back to FIG. 1, the storage unit 140 may store the ultrasound data acquired by the ultrasound data acquisition unit 120.

The display unit 150 may display the reference ultrasound image and the optimal sub ultrasound image. The display unit 150 may further display the sub ultrasound images.

Third Embodiment

Referring to FIG. 1, the medical device 110 may include the needle (not shown) and a fluid providing section (not shown). The needle may include a pipe (not shown) therein. The fluid providing section may be configured to provide the fluid to the pipe.

The ultrasound data acquisition unit 120 may include an ultrasound probe 210, the Tx signal generating section 220, the receiving section 230 and the ultrasound data forming section 240, as shown in FIG. 2.

The ultrasound probe 210 may include the plurality of elements (not shown) for reciprocally converting between ultrasound signals and electrical signals. The ultrasound probe 210 may be configured to transmit ultrasound signals to the living body based on each of scanlines (not shown). The ultrasound probe 210 may further receive the ultrasound echo signals from the living body and output the received signals. The received signals may be analog signals.

The Tx signal generating section 220 may be configured to control the transmission of the ultrasound signals. The Tx signal generating section 220 may be further configured to generate Tx signals in consideration of the elements and the focal points. In the embodiment, the Tx signal generating section 220 may form Tx signals for obtaining each of ultrasound images, sequentially. Thus, the ultrasound probe 210 may convert the Tx signals provided from the Tx signal generating section 220 into ultrasound signals, transmit the ultrasound signals to the living body, and receive the ultrasound echo signals from the living body to thereby output the received signals.

The beam former 230 may be configured to convert the received signals provided from the ultrasound probe 210 into digital signals. The beam former 230 may be further configured to apply delays to the digital signals in consideration of the elements and the focal points to output digital receive-focused signals.

The ultrasound data forming section 240 may be configured to form ultrasound data corresponding to each of the ultrasound images based on the digital receive-focused signals provided from the beam former 230. The ultrasound data forming section 240 may be further configured to perform signal processing (e.g., gain control, etc) upon the digital receive-focused signals.

Figure 7:
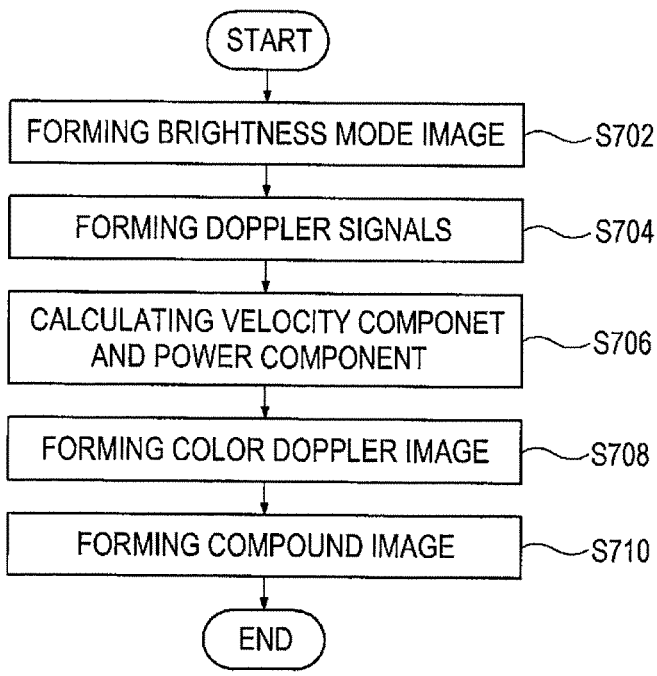
FIG. 7 is a flow chart showing a process of forming an optimal ultrasound image for interventional treatment in accordance with a third embodiment.

FIG. 7 is a flow chart showing a process of forming an optimal ultrasound image for interventional treatment in accordance with the third embodiment. The processing unit 130 may be configured to form at least one brightness mode image based on the ultrasound data provided from the ultrasound data acquisition unit 120, at step S702 in FIG. 7.

The processing unit 130 may be configured to form Doppler signals based on the ultrasound data provided from the ultrasound data acquisition unit 120, at step S704 in FIG. 7. The methods of forming the Doppler signals based on the ultrasound data are well known in the art. Thus, they have not been described in detail so as not to unnecessarily obscure the present invention.

The processing unit 130 may be configured to calculate velocity components and power components based on the Doppler signals, at step S706 in FIG. 7. The methods of calculate the velocity components and the power components based on the Doppler signals are well known in the art. Thus, they have not been described in detail so as not to unnecessarily obscure the present invention.

The processing unit 130 may be configured to form a color Doppler image corresponding to the fluid flow based on the velocity components and the power components, at step S708 in FIG. 7. The methods of forming the color Doppler image based on the velocity components and the power components are well known in the art. Thus, they have not been described in detail so as not to unnecessarily obscure the present invention.

The processing unit 130 may be configured to perform image compounding upon the brightness mode image and the color Doppler image to form a compound image, at step S710 in FIG. 7.

Optionally, the processing unit 130 may further detect a position of the medical device 110 from the brightness mode image based on the color Doppler mage, and perform the image processing for making prominence of the medical device 110 upon the brightness mode image based on the detected position.

Referring back to FIG. 1, the storage unit 140 may store the ultrasound data acquired by the ultrasound data acquisition unit 120. The storage unit 140 may further store the Doppler signals formed by the processing unit 130.

The display unit 150 may display the compound image formed by the processing unit 130. The display unit 150 may further display the brightness mode image formed by the processing unit 130. The display unit 150 may further display the color Doppler image formed by the processing unit 130.

Fourth Embodiment

Referring to FIG. 1, the medical device 110 may include the needle (not shown) for remove the lesion of the living body.

The ultrasound data acquisition unit 120 may include the ultrasound probe 210, the Tx signal generating section 220, the beam former 230 and the ultrasound data forming section 240 as shown in FIG. 2.

The ultrasound probe 210 may include the plurality of elements (not shown) for reciprocally converting between ultrasound signals and electrical signals. The ultrasound probe 210 may be configured to transmit ultrasound signals to the living body based on each of scanlines (not shown). The ultrasound probe 210 may be further configured to receive the ultrasound echo signals from the living body to thereby output the received signals.

The Tx signal generating section 220 may be configured to control the transmission of the ultrasound signals. The Tx signal generating section 220 may be further configured to generate Tx signals for obtaining each of ultrasound images in consideration of the elements and the focal points.

The beam former 230 may be configured to convert the received signals provided from the ultrasound probe 210 into digital signals. The beam former 230 may be further configured to apply delays to the digital signals in consideration of the elements and the focal points to output digital receive-focused signals.

The ultrasound data forming section 240 may be configured to form the ultrasound data corresponding to each of the ultrasound images based on the digital receive-focused signals provided from the beam former 230. The ultrasound data may include phase information. Also the ultrasound data may be radio frequency data. However, it should be noted herein that the ultrasound data may not be limited thereto. The ultrasound data forming section 240 may further perform signal processing (e.g., gain control, etc) upon the digital receive-focused signals.

Figure 8:
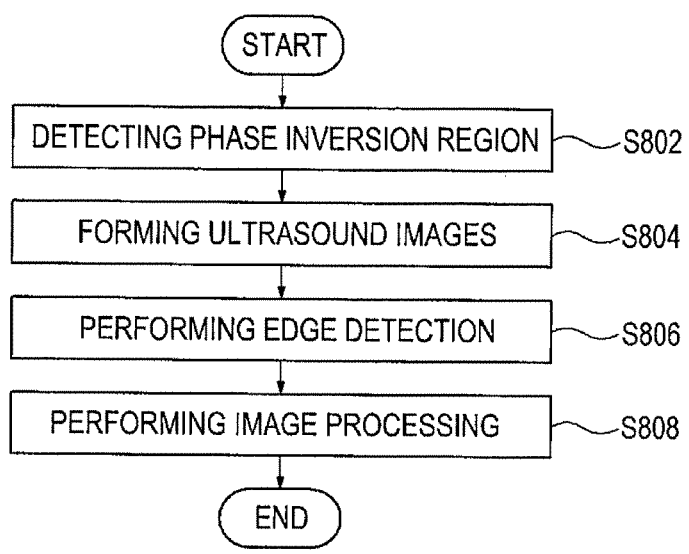
FIG. 8 is a flow chart showing a process of forming an optimal ultrasound image for interventional treatment in accordance with a fourth embodiment.

FIG. 8 is a flow chart showing a process of forming an optimal ultrasound image for interventional treatment in accordance with the fourth embodiment. The processing unit 130 may be configured to analyze the ultrasound data provided from the ultrasound data acquisition unit 120 to detect a region that phase inversion occurs, at step S802 in FIG. 8. Generally, the phase of sound wave is inverted at a reflection plane when the sound wave is transmitted from a softness medium to a hardness medium, or vice verse. Thus, the processing unit 130 may detect the phase inversion region at the reflection plane based on the phase inversion characteristic.

The processing unit 130 may be configured to form the ultrasound images based on the ultrasound images provided from the ultrasound data acquisition unit 120, at step S804 in FIG. 8. The ultrasound image may include a brightness mode image. However, it should be noted herein that the ultrasound image may not be limited thereto.

The processing unit 130 may be configured to perform edge detection upon the phase inversion region of the ultrasound images, at step S806 in FIG. 8. The edge may be detected by using an edge mask such as a Sobel mask, a Prewitt mask, a Robert mask, a Canny mask and the like. Also, the edge may be detected by using a structure tensor.

The processing unit 130 may be configured to perform an image processing upon the ultrasound data based on the detected edge, at step S808 in FIG. 8. In one embodiment, the processing unit 130 may perform the image processing for making prominence of the detected edge upon the ultrasound image.

Referring back to FIG. 1, the storage unit 140 may store the ultrasound data acquired at the ultrasound data acquisition unit 120.

The display unit 150 may display the ultrasound image formed at the processing unit 130. The display unit 150 may further display the image-processed ultrasound image.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A medical system, comprising:
   a medical device adapted to be inserted into a target object and configured to remove a lesion within the target object, the medical device comprising a needle including a pipe therein and a fluid provider configured to provide fluid to the pipe;
   an ultrasound data acquisition unit configured to transmit and receive ultrasound signals to and from the target object to output ultrasound data; and
   a processor in communication with the ultrasound data acquisition unit, the processor being configured to form a brightness mode image and a color Doppler image corresponding to flow of the fluid based on the ultrasound data, detect a position of the needle from the brightness mode image based on the color Doppler image and perform an image processing for making prominence of the brightness mode image based on the detected position of the needle,
   wherein the fluid provider, the ultrasound data acquisition unit, and the processor are implemented as hardware components.

2. The medical system of claim 1, wherein processor is configured to:
   form Doppler signals based on the ultrasound data;
   calculate velocity components and power components based on the Doppler signals; and
   form the color Doppler image corresponding to the flow of the fluid based on the velocity components and the power components.

3. The medical system of claim 2, wherein the processor is further configured to:
   perform an image compounding upon the brightness mode image and the color Doppler image to form compound image.

4. The medical system of claim 1, wherein the processor is further configured to:
   detect a phase inversion region based on the ultrasound data, wherein the phase inversion region is defined when a sound wave is transmitted from a softness medium to a hardness medium, or vice verse;
   perform edge detection upon the phase inversion region of the brightness mode image; and
   perform the image processing for making prominence upon the brightness mode image based on the detected edge.

5. A method of providing an ultrasound image for interventional treatment, comprising:
   a) inserting a medical device into a target object, wherein the medical device comprises a needle including a pipe therein and a fluid providing section configured to provide fluid to the pipe;
   b) transmitting and receiving ultrasound signals to and from the target object to output ultrasound data;
   c) forming a brightness mode image and a color Doppler image corresponding to flow of the fluid based on the ultrasound data;
   d) detecting a position of the needle from the brightness mode image based on the color Doppler image and:
   e) performing an image processing for making prominence of the brightness mode image based on the detected position of the needle.

6. The method of claim 5, wherein the step c) comprises:
   forming Doppler signals based on the ultrasound data;
   calculating velocity components and power components based on the Doppler signals; and
   forming the color Doppler image corresponding to the flow of the fluid based on the velocity components and the power components.

7. The method of claim 6, wherein the step e) further comprises:
   performing an image compounding upon the brightness mode image and the color Doppler image to form compound image.

8. The method of claim 5, wherein the step e) further comprises:
   detecting a phase inversion region based on the ultrasound data, wherein the phase inversion region is defined when a sound wave is transmitted from a softness medium to a hardness medium, or vice verse;
   performing edge detection upon the phase inversion region of the bright mode images; and
   performing the image processing for making prominence upon the brightness mode based on the detected edge.

* * * * *